United States Patent [19]

Takagawa et al.

[11] Patent Number: 5,444,172
[45] Date of Patent: Aug. 22, 1995

[54] PROCESS FOR PRODUCING A MONOALKENYL AROMATIC HYDROCARBON COMPOUND

[75] Inventors: Makoto Takagawa; Kenji Inamasa; Norio Fushimi; Akio Hashimoto; Takayo Sasaki, all of Tsukuba, Japan

[73] Assignee: Mitsubishi Gas Chemical Company, Inc., Tokyo, Japan

[21] Appl. No.: 170,493

[22] Filed: Dec. 20, 1993

[30] Foreign Application Priority Data

Feb. 22, 1993 [JP] Japan .................................. 5-031843
Sep. 1, 1993 [JP] Japan .................................. 5-217437

[51] Int. Cl.$^6$ .................................................. C07C 2/72
[52] U.S. Cl. .................................. 585/452; 585/438; 585/453; 585/463; 585/467
[58] Field of Search ............... 585/446, 452, 453, 463, 585/467, 435, 438

[56] References Cited

U.S. PATENT DOCUMENTS 4,990,717  2/1991  Sikkenga .............................. 585/429
5,043,507  8/1991  Fukao et al. ......................... 585/452

FOREIGN PATENT DOCUMENTS 0357031  3/1990  European Pat. Off. .

*Primary Examiner*—P. Achutamurthy
*Attorney, Agent, or Firm*—Frishauf, Holtz, Goodman & Woodward

[57] ABSTRACT

There is disclosed a process for producing a monoalkenylbenzene which comprises alkenylating a side chain of an aromatic hydrocarbon compound having at least one hydrogen atom bonded at $\alpha$-position of the side chain (such as xylene) with a conjugated diene having 4 or 5 carbon atoms (such as butadiene) in the presence of a catalyst produced by calcining the mixture of a basic potassium compound and alumina and then heat treating the calcined product together with metallic sodium in an atmosphere of an inert gas. According to the aforesaid process, an industrially useful monoalkenylbenzene can be produced in high yield at a low cost with enhanced safety.

18 Claims, No Drawings

PROCESS FOR PRODUCING A MONOALKENYL AROMATIC HYDROCARBON COMPOUND

BACKGROUND OF THE INVENTION

1. Field of the Invention

The present invention relates to a process for producing a monoalkenylbenzene. More particularly, it pertains to a process for producing a monoalkenylbenzene by subjecting an aromatic hydrocarbon compound having at least one hydrogen atom bonded at a-position of the side chain to side-chain alkenylation by the use of a conjugated diene having 4 or 5 carbon atoms. A monoalkenylbenzene is useful as the starting intermediate material for various organic compounds typified by high molecular monomers and pharmaceutical preparations. As an example, 5-(o-tolyl)-2-pentene that is produced from o-xylene and 1,3-butadiene can be converted into industrially useful 2,6-naphthalene-dicarboxylic acid by ring closure followed by dehydrogenation, isomerization and oxidation.

2. Description of Related Arts

As a process for producing a monoalkenylbenzene by subjecting an aromatic hydrocarbon compound to side-chain alkenylation by the use of a conjugated diene having 4 or 5 carbon atoms, there is known the process in which is employed as a catalyst an alkali metal such as sodium and potassium or an alloy thereof.

For example, German Patent No. 557514 discloses the use of metallic sodium as a catalyst in the above-mentioned process and Eberhardt et al. describes the use of metallic sodium supported on an alkaline earth metal oxide as a catalyst in J. Org. Chem., vol. 30 (1965), pp 82 to 84.

Likewise, there are disclosed the use of metallic potassium in Japanese Patent Publication No. 17973/1975, the use of a potassium/sodium alloy or a mixture of metallic potassium and metallic sodium in Japanese Patent Publication Nos. 17975/1975 and 8930/1976, and the use of metallic potassium supported on an alkali metal oxide or an alkaline earth metal oxide in U.S. Pat. No. 3,244,758 and the aforementioned J. Org. Chem., vol. 30 (1965), pp 82 to 84, each as the catalyst in the above-mentioned process.

There is also disclosed the use of the mixture obtained by heat treating a potassium compound and metallic sodium at 300° C. or a temperature not lower than 350° C. as the catalyst in the above-mentioned process in Japanese Patent Application Laid-Open Nos. 27929/1972 and 31935/1972.

Among the aforestated processes, the process in which is used as a catalyst metallic sodium with or without being supported on an alkaline earth metal oxide is impractical because of insufficiency in both catalytic activity and selectivity of reaction. The process in which is used as a catalyst, metallic potassium, a potassium/sodium alloy or a mixture of metallic potassium and metallic sodium exhibits a high catalytic activity but causes violent reaction of the catalyst with oxygen, moisture and the like. Therefore, an attempt to put the aforesaid process into industrial practice involves various problems on safety due to possible hazards such as fire and explosion.

Likewise, the process in which metallic potassium which is supported on the oxide of an alkali metal or an alkaline earth metal is used as a catalyst involves various problems on safety due to the use of the extremely combustible metallic potassium when put into industrial practice.

On the other hand, the process in which is used as a catalyst the mixture obtained by heat treating a potassium compound and metallic sodium at a high temperature is characterized in that metallic potassium or a potassium alloy is not employed, but can not be said to be necessarily practical because of insufficient catalytic activity and the necessity for treating the highly inflammable substance at a high temperature.

SUMMARY OF THE INVENTION

It is an object of the present invention to eliminate the various disadvantages of the conventional processes, that is, to provide a process with safety for producing a monoalkenylbenzene in high yield at a low cost in subjecting an aromatic hydrocarbon compound having at least one hydrogen atom bonded at $\alpha$-position of the side chain to side-chain alkenylation with a conjugated diene having 4 or 5 carbon atoms.

It is another object of the present invention to provide a catalyst for producing a monoalkenylbenzene in high yield at a low cost.

Other objects of the present invention will be obvious from the description of this text hereinafter disclosed.

Under the above-mentioned circumstances, intensive research and investigation were made by the present inventors in order to attain the above-described objects. As a result, it has been found by the present inventors that a monoalkenylbenzene can be produced with assured safety in high yield at a low cost by the use of a solid base-catalyst obtained by adding metallic sodium, in an atmosphere of an inert gas, to the carrier produced by calcining the mixture of a basic potassium compound and alumina, and subsequently heat treating the resultant product at the melting point of sodium or higher. The present invention has been accomplished on the basis of the above-mentioned finding.

The catalyst which is prepared according to the process of the present invention has remarkably high activity in the side-chain alkenylation reaction of an aromatic hydrocarbon compound with a conjugated diene, and sufficient activity of the catalyst is obtained even if the catalyst is prepared by heat treatment at a relatively low temperature provided that the temperature is not lower than the melting point of metallic sodium, that is, 97.8° C. In addition, even a relatively small amount of the catalyst enables the production of a monoalkenylbenzene in high yield and in high selectivity with facility in handling the catalyst.

By virtue of the extremely high activity of the catalyst according to the present invention, the alkenylation reaction proceeds satisfactorily even under exceptionally mild reaction conditions including atmospheric pressure and a temperature of 100° to 200° C.

Specifically, the present invention provides a process for producing a monoalkenylbenzene by alkenylating a side chain of an aromatic hydrocarbon compound having at least one hydrogen atom bonded to $\alpha$-position of the side chain by using a conjugated diene having 4 to 5 carbon atoms which process comprises effecting said alkenylation by the use of a catalyst composition produced by a method wherein the compound obtained by calcining the mixture of a basic potassium compound and alumina at 500° to 700° C. is heat treated along with metallic sodium at 100° to 300° C. in an atmosphere of an inert gas.

DESCRIPTION OF PREFERRED EMBODIMENTS

Examples of the specific aromatic hydrocarbon compounds having at least one hydrogen atom bonded at α-position of the side chain to be employed as the starting raw material in the present invention include monocyclic aromatic hydrocarbons such as monoalkylbenzenes enumerated by toluene; ethylbenzene; n-propylbenzene; isopropylbenzene; n-butylbenzene; sec-butylbenzene; and isobutylbenzene, dialkylbenzenes enumerated by o-, m- and p-xylenes; o-, m- and p-ethyltoluenes; and o-, m- and p-diethylbenzenes, trialkylbenzenes enumerated by mesitylene; and pseudocumene and polyalkylbenzenes enumerated by 1,2,3,5-tetramethylbenzene; 1,2,4,5-tetramethylbenzene; pentamethylbenzene; and hexamethylbenzene, and polycyclic aromatic hydrocarbons such as 1- and 2-methylnaphthalenes, dimethylnaphthalenes, alkyl tetrahydronaphthalenes and alkyl indanes.

As the conjugated dienes having 4 or 5 carbon atoms as another starting raw material, there are preferably used 1,3-butadiene; 1,3-pentadiene; and isoprene.

Examples of the basic potassium compound to be used in preparing the catalyst according to the present invention include potassium hydroxide, potassium carbonate, potassium phosphate, potassium hydrogencarbonate and potassium hydrogenphosphate. The use of a neutral potassium compound such as potassium sulfate and potassium nitrate can not achieve the excellent performance shown by the catalyst according to the present invention.

A basic potassium compound, when mixed with alumina, reacts therewith. When the mixture of the aforesaid two compounds is dried at 100° to 150° C., there is observed by X-ray diffraction, a peak assigned to AlOOH in addition to a peak assigned to alumina. It has been found that when the mixture is calcined at a higher temperature, new peaks emerge at $2\theta=32.4$ deg. and 58.5 deg. and grow with a rise of calcination temperature, whereas the peak assigned to AlOOH diminishes with a rise of calcination temperature and completely disappear at 500° C. and higher, wherein $\theta$ stands for Bragg angle. It has also been found that the growth and diminishment of each of the peaks as observed in X-ray diffraction are closely correlated with the catalytic activity and that it is important that the peaks at $2\theta=32.4$ deg. and 58.5 deg. be sufficiently grown and the peak assigned to AlOOH be negligible for the purpose of preparing the highly active catalyst.

The peaks at $2\theta=32.4$ deg. and 58.5 deg. are not observed in the X-ray diffraction of alumina or a basic potassium compound and thus originate from a substance formed by the interaction of alumina and the basic potassium compound. Such substance is assumed to be an aluminate of potassium, but there is not found a single aluminate of potassium which shows peaks at $2\theta=32.4$ deg. and 58.5 deg. in X-ray diffraction. Hence, the substance is presumed to be a mixture of a variety of aluminates.

As can be seen from the above-mentioned results, the calcination temperature after mixing a basic potassium compound with alumina exerts a pronounced influence on the catalyst performance, and it is the indispensable condition to carry out the calcination at 500° to 700° C., preferably 550° to 650° C.

A calcination temperature lower than 500° C. unfavorably leads to insufficiency in the growth of the peaks at $2\theta=32.4$ deg. and 58.5 deg, causing considerable amount of AlOOH to coexist. AlOOH is a kind of alumina hydrate and the primary contributor to deactivation of metallic sodium when mixed therewith. On the other hand, a calcination temperature higher than 700° C. unfavorably results in insufficiency in catalytic activity because of insufficient dispersion of metallic sodium at the time of preparing the catalyst by mixing therewith, even though the growth of the peaks at $2\theta=32.4$ deg. and 58.5 deg. is satisfactory. The use of a neutral potassium compound such as potassium nitrate and potassium sulfate in lieu of the basic potassium compound can not attain sufficient catalytic-activity and necessitates a large amount of catalyst made from the neutral potassium compound for the purpose of achieving satisfactory reaction performance.

In the case where the aforesaid neutral potassium compound is used in preparing the catalyst, neither the peak assigned to AlOOH in the drying step nor the peaks at $2\theta=32.4$ deg. and 58.5 deg. after calcination are observed. It is thought therefore, that the aforesaid neutral potassium compound hardly interacts with alumina and after calcination, the compound or the decomposition product thereof is only supported on the alumina, thereby failing to form the aluminate as obtained in the process according to the present invention. As an example, when potassium nitrate is used for preparing the catalyst, there is not observed the formation of the aluminate as obtained in the process of the present invention under the above-mentioned calcination conditions, presumably because the potassium nitrate is converted into oxides of potassium by calcination. In addition, the catalyst prepared by using calcined product of potassium nitrate and alumina is extremely poor in catalytic activity as compared with the catalyst according to the present invention, thereby necessitating a markedly larger amount of itself for the purpose of achieving the reaction performance comparable to that of the catalyst according to the present invention.

In the case of preparing the mixture of the basic potassium compound and alumina, either a wet system or a dry system is acceptable provided that both the compounds are sufficiently mixed with and dispersed in each other. However, a wet system is preferable for the purpose of homogeneous dispersion.

As the method of preparing the mixture by a wet system there is generally available a method in which alumina is mixed with and dispersed in the aqueous solution of the basic potassium hydroxide to form a mixed solution, followed by drying. In the case of using a potassium compound having a relatively low melting point such as potassium hydroxide, there is also available a method wherein both the compounds are mixed with heating at a temperature higher than the melting point of the potassium compound.

The mixing ratio by parts by weight of the basic potassium compound to alumina is 0.01 to 1, preferably 0.1 to 0.5 expressed in terms of metallic potassium vs. alumina.

An amount of the potassium compound less than the lower limit of the aforesaid mixing ratio leads to such disadvantages that a side reaction such as the isomerization of the alkenylbenzene to be produced is likely to occur, the deterioration of catalytic activity is accelerated, and an unreasonably large amount of the catalyst is needed to maintain the high activity of the catalyst, whereby the post-treatment after the reaction is complicated. On the other hand an amount thereof more than the above higher limit unfavorably makes it hardly possible to manifest the effect due to the use of the alumina, because a long time is required for obtaining a highly active catalyst in heating treatment together with metallic sodium and also a higher temperature is required for heat treatment.

The basic potassium compound to be used in the present invention may contain other salts such as a nitrate and sulfate up to the amount equimolar with potassium.

The catalyst according to the present invention is prepared by mixing the basic potassum compound with alumina, calcining the mixture to produce the carrier and subsequently mixing with heating the carrier and metallic sodium in an atmosphere of an inert gas. By the term "inert gas" as mentioned herein is meant a gas that is substantially nonreactive with the catalyst to be prepared under the preparation conditions for the catalyst, which inert gas is exemplified by nitrogen, helium and argon.

The catalyst to be used in the present invention is prepared at a heating temperature in the range of the melting point of metallic sodium to 500° C., desirably 100° to 300° C. The heating treatment time is usually in the range of 5 to 300 minutes.

Metallic sodium, when incorporated with potassium or the like, is brought into the form of liquid at a temperature lower than the melting point of sodium. In the above case, the catalyst can be prepared without any difficulty provided that the potassium-containing sodium is maintained at a temperature not lower than the temperature at which it is brought into the form of liquid.

In the case where the metallic sodium is not melted, the catalyst preparation results in difficulty in homogeneously dispersing metallic sodium in the carrier prepared from the basic potassium compound and alumina and in bringing metallic sodium into effective contact with the above carrier, thereby requring a long preparation time and rendering itself impractical. On the other hand, although the catalyst can be prepared at a temperature exceeding 500° C., it can not be said that handling of an inflammable substance at a high temperature is favorable in industrial practice.

The amount of the metallic sodium to be used in the preparation of the catalyst according to the present invention is determined so that the atomic ratio of metallic sodium to potassium atom in the potassium compound is 0.01 to 5, preferably 0.1 to 3. An amount of metallic sodium less than the above range unfavorably results in failure to sufficiently exert the effect due to the use of metallic sodium and the potassium compound, thereby necessitating an unreasonably large amount of the catalyst to assure the required catalytic activity. On the other hand, an amount thereof more than the above range leads to failure to sufficiently exert the effect due to the use of the carrier prepared from the basic potassium compound and alumina, thus causing unfavorable result from the viewpoint of safety and catalyst handling.

An alkali metal other than sodium such as potassium or an alkaline earth metal, even if contained in the metallic sodium for preparing the catalyst, does not cause any problem provided that the amount of the metallic sodium is within the above-described range.

In employing the catalyst according to the present invention thus obtained in the alkenylation reaction, various reaction systems are available and exemplified by batchwise or semi-batchwise system in which the starting raw material is fed batchwise or semi-batchwise into a reactor which has previously been fed with the catalyst; complete mixing system in which the catalyst and starting raw material are continuously fed into a reactor; and flow system through fixed bed in which the starting raw material is allowed to flow through a reactor which has previously been packed with the catalyst. The reaction system should be suitably selected in accordance with the type of the objective reaction product. In general, the selectivity to the objective monoalkenylbenzene can be enhanced by the system wherein an aromatic hydrocarbon as one of the starting raw materials is allowed to be present in excess against a conjugated diene. For the purpose of enhancing the selectivity, a semi-batchwise system is preferable in which a conjugated diene is continuously fed into the reaction system. In the case of continuous reaction by a complete mixing system or a flow system through a fixed bed, it is preferable for enhancing the selectivity to adopt the reaction system capable of lowering the concentration of a conjugated diene in the reactor such as the system in which a conjugated diene is fed into each stage of a multistage reactor to be adopted.

The reaction between the aromatic hydrocarbon and the conjugated diene in the process according to the present invention is carried out under the conditions in which the aromatic hydrocarbon as the starting raw material and the objective product are substantially in the form of liquid.

The reaction temperature in the process according to the present invention is in the range of 50° to 300° C., preferably 100° to 200° C. A temperature lower than the above lower limit can cause the reaction to take place, but results in failure to attain a sufficient reaction rate; and besides tends to lower the selectivity, while that higher than the above higher limit unfavorably leads to an increased amount of by-product such as tar components. The reaction is more preferably carried out at the reflux temperature or lower when it is lower than 200° C. from the viewpoint of keeping the reaction conditions in which the starting raw material and the objective product are substantially in the form of liquid.

The reaction pressure is not specifically limited insofar as the aromatic hydrocarbon as the starting raw material and the objective product are present substantially in the form of liquid. It is in the range of 0.05 to 5 absolute atmospheric pressure ($0.05 \times 10^5$ to $5.07 \times 10^5$ Pa), preferably 0.1 to 2 absolute atmospheric pressure ($0.10 \times 10^5$ to $2.03 \times 10^5$ Pa).

In the process according to the present invention, the molar ratio of the conjugated diene having 4 to 5 carbon atoms as another starting raw material to the aromatic hydrocarbon as a starting raw material is generally 0.01 to 1, preferably 0.03 to 0.5. A molar ratio thereof higher than the above higher limit unfavorably causes an increase in the formation of the compound in which the monoalkenylbenzene thus produced is further reacted with the excess diene to allow the addition of at least two molecules of the diene to one molecule of the aromatic hydrocarbon and the likelihood of diene polymerization, whereby the selectivity to the objective compound is undesirably worsened.

The amount of the catalyst to be used in the process according to the present invention is 0.01% or more, preferably 0.05% or more by weight based on the amount of the aromatic hydrocarbon as a starting raw material.

As described hereinbefore, the reaction system is selected from a batchwise system, a semi-batchwise system, a complete mixed flow system and the like in putting the process of the invention into practice. There is usually adopted 0.1 to 10 hours as the reaction time in a batchwise and a semi-batchwise system and as the retention time in a complete mixing system. In the case of a flow system through a fixed bed, a liquid hourly space velocity (LHSV) for the aromatic hydrocarbon in the range of 0.1 to 10 h$^{-1}$ is usually selected.

In the case of carrying out the reaction a with suspended catalyst, the separation of the reaction liquid from the catalyst after the reaction can easily be performed by any of the conventional methods including sedimentation, centrifugal separation and filtration. The separated catalyst may be circulated through the reaction system or subjected to the necessary step such as removing organic substances attached thereto by combustion with air and cleaning with water, followed by circulation through a catalyst preparation step.

The process according to the present invention is capable of producing a monoalkenylbenzene having industrial availability from an aromatic hydrocarbon compound and a conjugated diene in high reaction performance at a low cost with enhanced safety, thus rendering itself extremely significant from the industrial viewpoint.

In the following, the present invention will be described in more detail with reference to the examples, but shall not be limited thereto.

EXAMPLE 1

To an aqueous solution of 20.85 g of potassium hydroxide (KOH) was added 58 g of alumina powder (Al$_2$O$_3$) (Model DN-1A produced by Mizusawa Industrial Chemicals, Ltd.) under stirring for mixing at room temperature for one hour. The mixture was dried overnight at 115° C. and then calcined in air at 550° C. Thereafter, 5 g of the calcined mixture was stirred at 150° C. in a nitrogen atmosphere and incorporated with 0.60 g of metallic sodium, followed by stirring for 30 min. at the resulting temperature (150° C.). The powdery catalyst thus obtained was incorporated, in a stream of nitrogen, with 1000 g of o-xylene that had been dehydrated with molecular sieve, and subsequently the resultant mixture was heated to 140° C. Then 50 g of 1,3-butadiene was introduced into the reaction system over a period of one hour with stirring under atmospheric pressure to carry out the side-chain alkenylation reaction. After cooling the reaction system, the catalyst was deactivated by adding isopropyl alcohol thereto and then the reaction liquid was sampled for analysis by gas chromatography. The reaction results are given in Table 1.

EXAMPLES 2 TO 4

The procedure in Example 1 was repeated to prepare the catalysts and carry out the reaction by the use thereof except for alteration in the mixing ratio of KOH to Al$_2$O$_3$, calcination temperature in preparing the carrier from KOH and Al$_2$O$_3$, amount of the carrier, amount of metallic sodium, treatment temperature and treatment time as described in Table 1. The reaction results are given in Table 1.

The treatment temperature and the treatment time are the temperature and the time, respectively in mixing the metallic sodium with the carrier prepared from KOH and Al$_2$O$_3$.

EXAMPLE 5

The procedure in Example 1 was repeated to prepare the catalyst and carry out the reaction except that 30 g of potassium carbonate was employed in place of 20.85 g of KOH. The reaction results are given in Table 1.

EXAMPLE 6

The procedure in Example 1 was repeated to prepare the catalyst and carry out the reaction except that 22 g of potassium hydrogencarbonate was used in place of 20.85 g of KOH, The reaction results are given in Table 1.

EXAMPLE 7

The procedure in Example 1 was repeated to prepare the catalyst and carry out the reaction except that 10.4 g of KOH was used and 7,0 g of NaOH was added. The reaction results are given in Table 1.

EXAMPLE 8

The procedure in Example 1 was repeated to prepare the catalyst and carry out the reaction except that 1,3-butadiene was fed in an amount of 70 g instead of 50 g. The reaction results are given in Table 1.

COMPARATIVE EXAMPLE 1

The procedure in Example 1 was repeated to prepare the catalyst and carry out the reaction except that 14.9 g of sodium hydroxide (NaOH) was used in place of 20.85 g of potassium hydroxide (KOH). The reaction results are given in Table 1.

COMPARATIVE EXAMPLE 2

The procedure in Example 1 was repeated to prepare the catalyst and carry out the reaction except that 37.6 g of potassium nitrate was used in place of 20.85 g of KOH. The reaction results are given in Table 1.

COMPARATIVE EXAMPLES 3 AND 4

The procedure in Example 1 was repeated to prepare the catalyst and carry out the reaction except that the calcination temperature of the mixture of KOH and Al$_2$O$_3$ was altered. The reaction results are given in Table 1.

COMPARATIVE EXAMPLE 5

10 g of potassium carbonate powder that had been calcined at 550° C. was heated to 200° C. in nitrogen, incorporated with 1.0 g of metallic soidum with stirring and further heated at the resulting temperature for 120 minutes to prepare the catalyst. After allowing the catalyst to cool, the reaction was performed in the same manner as in Example 1. The reaction results are given in Table 1.

COMPARATIVE EXAMPLE 6

The procedure in Example 1 was repeated to carry out the reaction except that 5.0 g of metallic sodium was used as the catalyst. The reaction results are given in Table 1.

COMPARATIVE EXAMPLE 7

The procedure in Example 1 was repeated to carry out the reaction except that 1.0 g of metallic potassium was used as the catalyst. The reaction results are given in Table 1.

TABLE 1

|  | K-compound ratio by wt*1 | Calcination temperature (°C.) | Usage of*2 mixture (g) | Amount of metallic Na (g) (Na/K atomic ratio) | Treatment*3 temperature (°C.) | Treatment*4 time (min.) | OTP*5 yield (%) |
| --- | --- | --- | --- | --- | --- | --- | --- |
| Example 1 | KOH(0.25) | 550 | 5.0 | 0.60(1.06) | 150 | 30 | 89.7 |
| Example 2 | KOH(0.45) | 600 | 5.0 | 0.50(0.58) | 130 | 60 | 90.9 |
| Example 3 | KOH(0.25) | 650 | 10.0 | 0.30(0.26) | 150 | 60 | 88.1 |
| Example 4 | KOH(0.35) | 510 | 5.0 | 1.00(1.38) | 180 | 30 | 91.5 |
| Example 5 | K₂CO₃(0.29) | 550 | 5.0 | 0.60(0.94) | 150 | 30 | 90.3 |
| Example 6 | KHCO₃(0.24) | 550 | 5.0 | 0.60(1.09) | 150 | 30 | 90.6 |
| Example 7 | KOH(0.12) NaOH(0.07) | 550 | 5.0 | 0.60(2.03) | 150 | 30 | 89.8 |
| Example 8 | KOH(0.25) | 550 | 5.0 | 0.60(1.06) | 150 | 30 | 82.7 |
| Comparative Example 1 | NaOH(0.15) | 550 | 5.0 | 0.60(0.72)*6 | 150 | 30 | 2.0 |
| Comparative Example 2 | KNO₃(0.25) | 550 | 5.0 | 0.60(1.06) | 150 | 30 | 50.7 |
| Comparative Example 3 | KOH(0.25) | 380 | 5.0 | 0.60(1.06) | 150 | 30 | 17.7 |
| Comparative Example 4 | KOH(0.25) | 800 | 5.0 | 0.60(1.06) | 150 | 30 | 67.3 |
| Comparative Example 5 | K₂CO₃(100) | 550 | 10.0 | 1.00(0.30) | 200 | 120 | 75.8 |
| Comparative Example 6 | — | — | — | 5.0 | — | — | 5.3 |
| Comparative Example 7 | — | — | — | K 1.0 | — | — | 83.2 |

*1Ratio by weight of alkali metal in alkali metal compound to Al₂O₃
*2Calcined product of mixture of alkali metal compound and alumina
*3Temperature in mixing metallic sodium with the carrier prepared from KOH and Al₂O₃
*4Period of time in mixing metallic sodium with the carrier prepared from KOH and Al₂O₃
*5OTP: 5-(o-tolyl)-2-pentene
*6As for Comparative Example 1, atomic ratio of introduced metallic sodium to sodium in the carrier prepared from NaOH and Al₂O₃

EXAMPLE 9

The powdery catalyst that had been prepared in the same manner as in Example 1 was incorporated, in a stream of nitrogen, with 1000 g of o-xylene that had been dehydrated with molecular sieve, and subsequently the resultant mixture was heated to 150° C. Subsequently 50 g of 1,3-butadiene was introduced into the reaction system with vigorous stirring for one hour to carry out the reaction. The reaction product was cooled and allowed to stand to sediment the catalyst powder. The resultant reaction liquid was taken out in almost entire amount by means of decantation and sampled for analysis by gas chromatography. The reaction results are given in Table 2.

EXAMPLE 10

The catalyst slurry that had been used for the reaction and left after the recovery of almost entire amount of the reaction liquid in Example 9 was incorporated, in a stream of nitrogen, with 1000 g of o-xylene and the mixture was heated to 150° C. Subsequently 50 g of 1,3-butadiene was introduced into the reaction system over a period of one hour with vigrous stirring to proceed with reaction. The procedure was repeated 4 times to proceed with the reaction in the same manner by the use of the catalyst left each time after the reaction liquid was taken out in almost entire amount by means of decantation, and thereafter, the catalyst was deactivated by adding isopropyl alcohol thereto and then the reaction liquid was sampled for analysis by gas chromatography. The reaction results are given in Table 2.

EXAMPLE 11

The powdery catalyst that had been prepared in the same manner as in Example 1 was incorporated, in a stream of nitrogen, with 1000 g of m-xylene that had been dehydrated with molecular sieve, and subsequently the resultant mixture was heated to 150° C. Subsequently 50 g of 1,3-butadiene was introduced into the reaction system over a period of one hour with vigorous stirring to carry out the reaction. After cooling the reaction system, the catalyst was deactivated by adding isopropyl alcohol thereto and then the reaction liquid was sampled for analysis by gas chromatography. The reaction results are given in Table 2.

EXAMPLES 12 AND 13

The procedure in Example 11 was repeated to carry out the reaction except that p-xylene or ethylbenzene was employed in place of m-xylene. The reaction results are given in Table 2.

TABLE 2

| | Aromatic hydrocarbon as starting material | Objective product | Yield (%) |
| --- | --- | --- | --- |
| Example 9 | o-xylene | 5-(o-tolyl)-2-pentene | 89.1 |
| Example 10 | o-xylene | 5-(o-tolyl)-2-pentene | 88.6 |
| Example 11 | m-xylene | 5-(m-tolyl)-2-pentene | 86.0 |
| Example 12 | p-xylene | 5-(p-tolyl)-2-pentene | 84.3 |
| Example 13 | ethylbenzene | 5-phenyl-2-hexene | 82.8 |

What is claimed is

1. A process for producing a monoalkenyl aromatic hydrocarbon compound comprising alkenylating a side chain of an aromatic hydrocarbon compound having at least one hydrogen atom bonded to an α-position of the side chain with a conjugated diene having 4 to 5 carbon atoms in the presence of a catalyst composition produced by calcining a mixture of a basic potassium compound and alumina at 550° to 650° C. to form a calcined mixture and heat treating the calcined mixture with metallic sodium at 100° to 300° C. in an inert gas atmosphere.

2. The process according to claim 1 wherein the compound obtained by calcining the mixture of a basic potassium compound and alumina is a substance having diffraction peaks at 2θ=32.4 degrees and 58.5 degrees wherein $\theta$ represents a Bragg angle, in addition to the diffraction peak assigned to alumina when analyzed by X-ray diffraction.

3. The process according to claim 1 wherein the basic potassium compound and the alumina are present in a mixing ratio of 0.01 to 1 expressed in terms of parts by weight of metallic potassium in said compound based on alumina.

4. The process according to claim 1 wherein the mixture of the basic potassium compound and alumina is prepared by a method in which alumina is mixed with and dispersed in an aqueous solution of the basic potassium compound to form a mixed solution and the basic potassium compound is potassium hydroxide.

5. The process according to claim 1 wherein the metallic sodium is present in a ratio of 0.01 to 5 expressed in terms of an atomic ratio of sodium to potassium atoms in the basic potassium compound.

6. The process according to claim 1 wherein the basic potassium compound is at least one compound selected from the group consisting of potassium hydroxide, potassium carbonate and potassium hydrogencarbonate.

7. The process according to claim 1 wherein the heat treatment is effected for 5 to 300 minutes.

8. The process according to claim 1 wherein the alkenylation is carried out at a reaction temperature of 100° C. to the reflux temperature under a reaction pressure of at most $2.03 \times 10^5$ Pa.

9. The process according to claim 6 wherein the aromatic hydrocarbon compound is selected from the group consisting of toluene, ethylbenzene, n-propylbenzene, isopropylbenzene, n-butylbenzene, sec-butylbenzene, isobutylbenzene, o-xylene, m-xylene, p-xylene, o-ethyltoluene, m-ethyltoluene, p-ethyltoluene, o-diethylbenzene, m-diethylbenzene, p-diethylbenzene, mesitylene, pseudocumene, 1,2,3,5-tetramethylbenzene, 1,2,4,5-tetramethylbenzene, pentamethylbenzene, hexamethylbenzene, 1-methylnaphthalene, 2-methylnaphthalene, dimethylnaphthalene, alkyl tetrahydronaphthalene and alkyl indane.

10. The process according to claim 9 wherein the conjugated diene is selected from the group consisting of 1,3-butadiene; 1,3-pentadiene; and isoprene.

11. The process according to claim 10 wherein the basic potassium compound and the alumina are present in a weight ratio of 0.1 to 0.5 expressed in terms of metallic potassium and alumina.

12. The process according to claim 11 wherein the metallic sodium is present in a ratio of 0.1 to 3 expressed in terms of an atomic ratio of sodium to potassium atoms in the basic potassium compound.

13. The process according to claim 12 wherein the alkenylation is carried out at a temperature of 50° to 300° C.

14. The process according to claim 13 wherein the alkylation is carried out at a pressure of 0.05 to 5 absolute atmospheric pressure.

15. The process according to claim 14 wherein the conjugated diene and the monoalkenyl aromatic hydrocarbon compound are in a molar ratio of 0.01 to 1.

16. The process according to claim 15 wherein the catalyst in present in an amount of 0.01 weight % or more based on the amount of the monoalkenyl aromatic hydrocarbon compound.

17. The process according to claim 16 wherein the alkenylation is carried out for 0.1 to 10 hours at a liquid hourly space velocity of 0.1 to 10 hours$^{-1}$.

18. The process according to claim 17, wherein the alkenylating is carried out at a temperature of 100° to 200° C. and at a pressure of 0.1 to 2 absolute atmospheric pressure; the conjugated diene and the monoalkylene aromatic hydrocarbon compound are in a molar ratio of 0.03 to 0.5; and the catalyst is present in an amount of 0.05 weight % or more based on the amount of the monoalkenyl aromatic hydrocarbon compound.

* * * * *